(12) United States Patent
Venkatasubramanian et al.

(10) Patent No.: US 9,808,342 B2
(45) Date of Patent: Nov. 7, 2017

(54) BALLOON SIZING DEVICE AND METHOD OF POSITIONING A PROSTHETIC HEART VALVE

(71) Applicant: St. Jude Medical, Cardiology Division, Inc., St. Paul, MN (US)

(72) Inventors: Ramji T. Venkatasubramanian, Maplewood, MN (US); Peng Peng, Falcon Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 798 days.

(21) Appl. No.: 13/788,663

(22) Filed: Mar. 7, 2013

(65) Prior Publication Data

US 2014/0012367 A1 Jan. 9, 2014

Related U.S. Application Data

(60) Provisional application No. 61/667,578, filed on Jul. 3, 2012.

(51) Int. Cl.
*A61F 2/24* (2006.01)
*A61B 5/02* (2006.01)
*A61B 5/107* (2006.01)

(52) U.S. Cl.
CPC ........ *A61F 2/2496* (2013.01); *A61B 5/02007* (2013.01); *A61B 5/1076* (2013.01); *A61B 2562/028* (2013.01); *A61F 2250/0096* (2013.01)

(58) Field of Classification Search
CPC ........... A61F 2/2496; A61F 2250/0096; A61B 2/02007; A61B 2/1076; A61B 5/02007; A61B 5/10765; A61B 2562/028
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2013/048211 dated Dec. 4, 2013.

(Continued)

*Primary Examiner* — Anh Dang
(74) *Attorney, Agent, or Firm* — Lerner, David, Littenberg, Krumholz & Mentlik, LLP (57) ABSTRACT

A sizing device for a collapsible prosthetic heart valve, the sizing device includes a collapsible and expandable balloon having a proximal end, a distal end. At least one microelectromechanical sensor is coupled to the balloon, the at least one sensor being capable of measuring information related to size and stiffness of tissue.

11 Claims, 9 Drawing Sheets

(56) References Cited

U.S. PATENT DOCUMENTS

| | | |
|---|---|---|
| 5,480,423 A | 1/1996 | Ravenscroft et al. |
| 5,509,411 A * | 4/1996 | Littmann .............. A61B 5/0422 600/381 |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0102722 A1 * | 5/2004 | Naghavi .................. A61B 5/01 600/587 |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0009746 A1 | 1/2008 | Forster et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0181556 A1 * | 7/2008 | Borgos .................. A61B 5/022 385/13 |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087782 A1 * | 4/2010 | Ghaffari .............. A61B 1/00082 604/103.01 |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0237940 A1 | 9/2011 | Raleigh |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |

(56) References Cited

FOREIGN PATENT DOCUMENTS

| | | | |
|---|---|---|---|
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2006073626 | A2 | 7/2006 |
| WO | 2007016260 | A2 | 2/2007 |
| WO | 2007071436 | A2 | 6/2007 |
| WO | 2008042347 | A2 | 4/2008 |
| WO | 2008070797 | A2 | 6/2008 |
| WO | 2009/042196 | A2 | 4/2009 |
| WO | 2010008548 | A2 | 1/2010 |
| WO | 2010008549 | A1 | 1/2010 |
| WO | 2010070633 | A1 | 6/2010 |
| WO | 2010096176 | A1 | 8/2010 |
| WO | 2010098857 | A1 | 9/2010 |
| WO | 2011103107 | A1 | 8/2011 |

OTHER PUBLICATIONS

Catheter-implanted prosthetic heart valves, Knudsen, L.L., et al., The International Journal of Artificial Organs, vol. 16, No. 5 1993, pp. 253-262.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Quaden et al., "Percutaneous aortic valve replacement: resection before implantation", pp. 836-840, European J. of Cardio-thoracic Surgery, 27 (2005).

Ruiz, Carlos, Overview of PRE-CE Mark Transcatheter Aortic Valve Technologies, Euro PCR, dated May 25, 2010.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

* cited by examiner

BALLOON SIZING DEVICE AND METHOD OF POSITIONING A PROSTHETIC HEART VALVE

CROSS REFERENCE TO RELATED APPLICATION

The application claims the benefit of the filing date of U.S. Provisional Patent Application No. 61/667,578 filed Jul. 3, 2012, the disclosure of which is hereby incorporated herein by reference.

BACKGROUND OF THE INVENTION

The present invention relates to heart valve replacement and, in particular, to collapsible prosthetic heart valves. More particularly, the present invention relates to devices and methods for sizing and positioning of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional delivery devices for self-expanding valves, clinical success of the valve is dependent on accurate deployment, anchoring and acceptable valve performance. Inaccurate sizing and positioning increases risks such as valve migration, which may result in severe complications due to obstruction of the left ventricular outflow tract and may even result in patient death. Additionally, calcification of the aortic valve may affect performance. Specifically, the degree of calcification may be important for patient selection criteria for valve implantation. Calcification has also been suggested as playing a role in anchoring transcathether implants. The interaction between the implanted valve and the calcified tissue is believed to be relevant to anchoring the valve in place and preventing valve migration.

Without being bound to any particular theory, it is believed that improper anchoring of the valve may occur due to a mismatch between the size of the native annulus and the size of the prosthetic valve (e.g., using a small size valve in a large annulus), lower calcification levels in the native tissue than actually predicted, or improper positioning of the valve resulting in insufficient expansion of the valve diameter. Moreover, overestimation of the annulus size may cause an oversized valve to be implanted, leading to local complications in the aortic root, including coronary orifice obstruction, aortic dissection and heart blockage. Additionally, oversized valves may cause extended compression and/or stent deformation that affects valve durability.

In addition, incorrect sizing of a valve due to anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the likelihood of removal. Methods and devices are also desirable that would reduce the likelihood of valve migration caused by improper anchoring.

Current methods for estimating the size of a patient's anatomy include imaging techniques such as transthoracic echocardiograms, trans-esophageal echocardiograms and angiography. These imaging methods are not standardized and may yield inconsistent results due to the elliptical shape of the target anatomy. Additionally, none of these techniques allow for contact forces between the annulus and stent to be measured and, thus they do not account for calcification.

There therefore is a need for further improvements to the devices, systems, and methods for transcatheter delivery and positioning of collapsible prosthetic heart valves. Specifically, there is a need for further improvements to the devices, systems, and methods for accurately measuring the native annulus dimensions and calcification levels in a patient. Such accurate measurement will help to reduce the risks associated with valve migration and improper valve positioning. Among other advantages, the present invention may address one or more of these needs.

SUMMARY OF THE INVENTION

In one embodiment, a sizing device for a collapsible prosthetic heart valve may include a collapsible and expandable balloon and at least one microelectromechanical sensor attached to the balloon, the at least one sensor being capable of measuring a property of tissue.

In some example, the device may include a conduit in fluid communication with the inside of the balloon for delivering a fluid to inflate the balloon. The balloon may include at least one of PET, Nylon, polyurethane or a thermoplastic elastomer. The at least one sensor may be capable of measuring data relating to native valve annulus diameter. The data may relate to the extent of calcification of tissue and may utilize capacitance to measure the information. The at least one sensor may include a piezoelectric material. The at least one sensor may include a polymer such as polydimethylsiloxane or a polyimide. The at least one sensor may also include a fabric. In some examples, the device may include a plurality of sensors arranged about the periphery of the balloon.

In another embodiment, a sizing device for a collapsible prosthetic heart valve includes a plurality of microelectromechanical sensors coupled end-to-end to form a collapsible and expandable balloon, the plurality of sensors being capable of measuring a property of tissue. The plurality of sensors may be capable of measuring data relating to native valve annulus diameter. The plurality of sensors may be capable of measuring data relating to the extent of calcification of tissue.

A method for determining the proper fitment of a heart valve within a native aortic annulus may include the steps of introducing a sizing device to the native annulus, the sizing device including (i) a collapsible and expandable balloon, and (ii) at least one microelectromechanical sensor attached to the balloon, expanding the diameter of the balloon within the native annulus, and acquiring data related to a property of tissue using the at least one microelectromechanical sensor.

In some example, the data may relate to an annulus diameter. The data may relate to an extent of calcification. In some examples, the method further includes a conduit in fluid communication with the inside of the balloon for inflating the balloon, and wherein expanding the diameter of the sizing device comprises injecting a fluid through the conduit to the inside of the balloon. The method may further include the step of deflating the balloon and removing the sizing device from the native annulus.

BRIEF DESCRIPTION OF THE DRAWINGS

Various embodiments of the present invention are described herein with reference to the drawings, wherein.

Various embodiments of the present invention will now be described with reference to the appended drawings. It is appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the portion or end of the heart valve closest to the heart when the heart valve is implanted in a patient, whereas the term "distal," when used in connection with a prosthetic heart valve, refers to the portion or end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1:
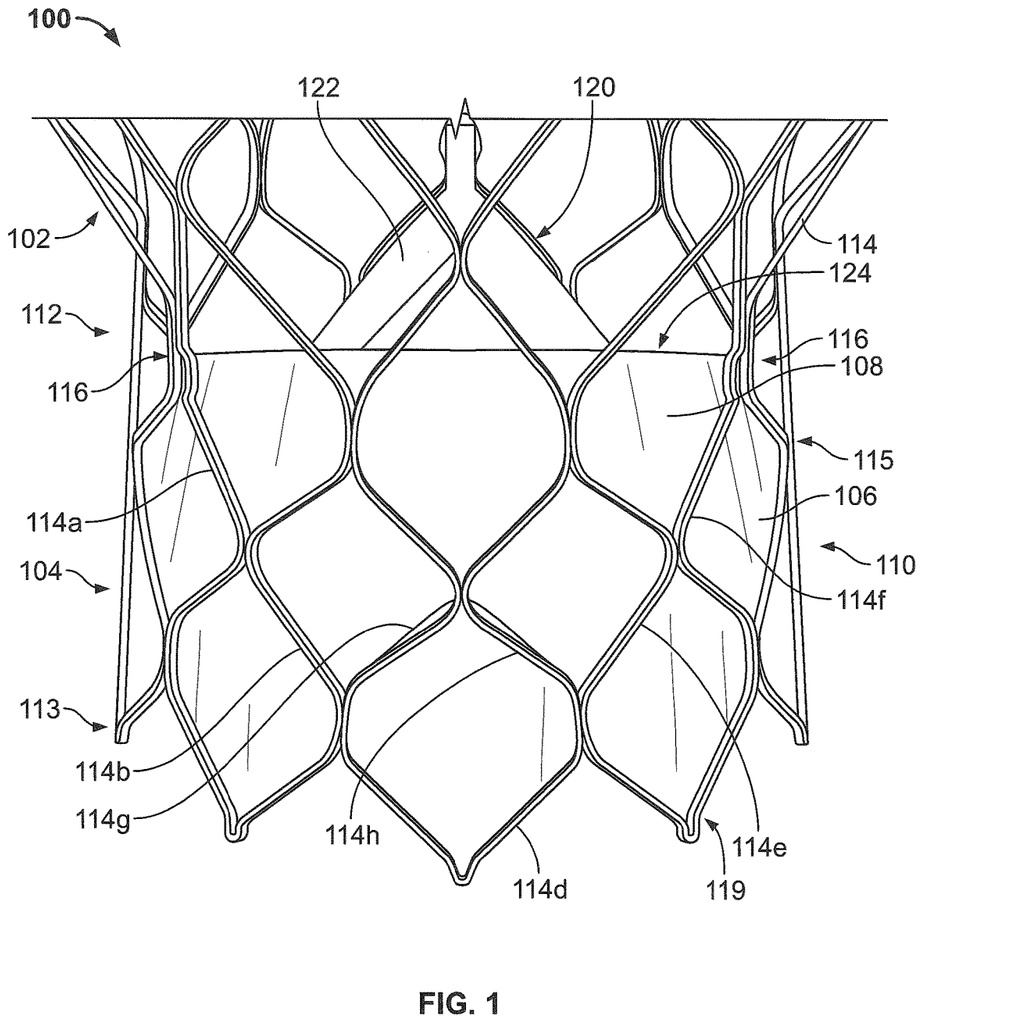
FIG. 1 is a side elevational view of a conventional prosthetic heart valve.

FIG. 1 shows a conventional collapsible prosthetic heart valve 100. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for other cardiac applications.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the cuff 106 or the stent 102 by any suitable attachment means, such as suturing, stapling, adhesives or the like. For example, the first edge 122 of each leaflet 108 may be attached to the cuff 106, and the cuff may in turn be attached to the stent 102. Alternatively, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the cuff 106 or to the stent 102 along at least some struts 114 of the stent to enhance the structural integrity of the valve assembly 104. As a consequence of this attachment, the struts 114 help support the leaflets 108 of the valve assembly 104 and may therefore reduce the strain in the leaflet-cuff junction.

In operation, the embodiment of the prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed inside the delivery device in the collapsed condition. The delivery device may be introduced into a patient using a transfemoral, transapical, transseptal or other approach. Once the delivery device has reached the target site, the user may deploy the prosthetic heart valve. Upon deployment, the prosthetic heart valve expands, preferably into secure engagement within the native aortic annulus. When the prosthetic heart valve is properly positioned inside the heart, it works as a one-way valve, allowing blood to flow in one direction and preventing blood from flowing in the opposite direction.

Problems may be encountered when implanting the prosthetic heart valve. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid disease, and/or valve insufficiency could not be treated well, if at all, with the current collapsible valve designs.

The reliance on evenly calcified leaflets for proper valve placement and seating could lead to several problems, such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

Figure 2A:
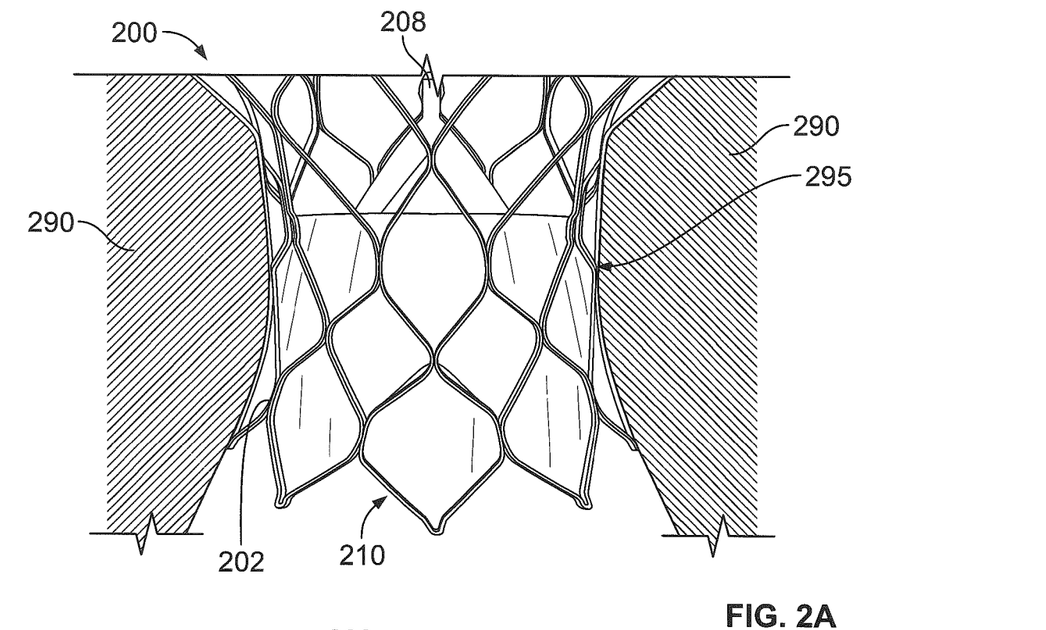
FIG. 2A is a highly schematic side elevational view of a prosthetic heart valve having poor fitment in a native valve annulus.

FIG. 2A illustrates a prosthetic heart valve 200 having poor fitment within native valve annulus 290. Specifically, as seen in FIG. 2A, the annulus section 210 of the stent 202 is distorted near deformed portion 295. Improper fitment of the prosthetic heart valve 200 may lead to any of the problems discussed above. In addition, as the stent 202 of collapsible prosthetic heart valve 200 distorts during implantation, during beating of the heart, or because of irregularities in the patient's anatomy or the condition of the native valve, such distortion may be translated to the valve assembly, such that not all of the valve leaflets 208 meet to form effective coaptation junctions. This can result in leakage or regurgitation and other inefficiencies which can reduce cardiac performance. Moreover, if the prosthetic valve 200 is not placed optimally and the valve leaflets 208 are not coapting as intended, other long term effects, such as uneven wear of the individual leaflets 208, can be postulated. Such improper fitment may be due to poor positioning, disregard for calcification or use of the wrong valve size.

Figure 2B:
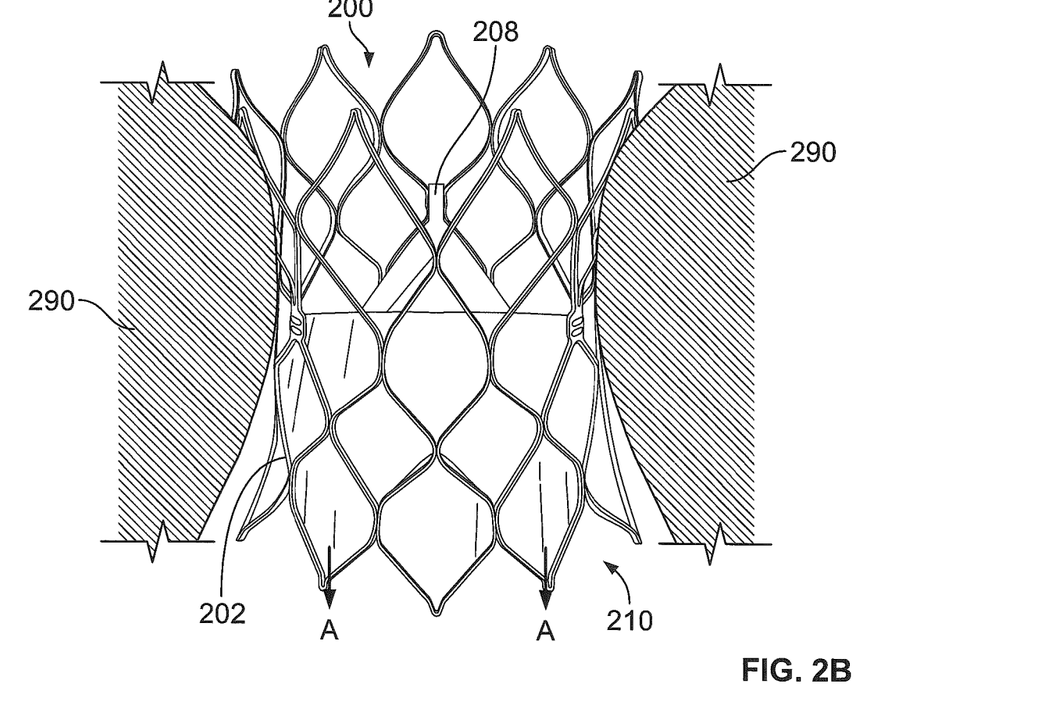
FIG. 2B is a highly schematic side elevational view of a prosthetic heart valve that has migrated from its implantation position in the native annulus.

Poor positioning, disregard for calcification or the use of the wrong valve size may also cause heart valve migration. As seen in FIG. 2B, prosthetic heart valve 200 has partially translated into the ventricle from its intended location at native valve annulus 290, a condition that may lead to a host of problems as discussed above. Even a small shift in position as indicated by arrows "A" may cause inadequate sealing and improper valve function. Migration may also result in regurgitation of blood passing through the valve.

In order to avoid these problems, a valve sizing device may be used to accurately determine the annulus diameter and the calcification levels in the aortic valve. The valve sizing device may be deployed first within the native valve sinus to determine the size, shape and condition of the sinus. After obtaining sufficient measurements, the valve sizing device may be removed from the native valve sinus and a suitable prosthetic heart valve may be chosen based on the obtained measurements. The selected prosthetic heart valve may then be implanted with a reduced risk of deformation and/or migration.

Figure 3A:
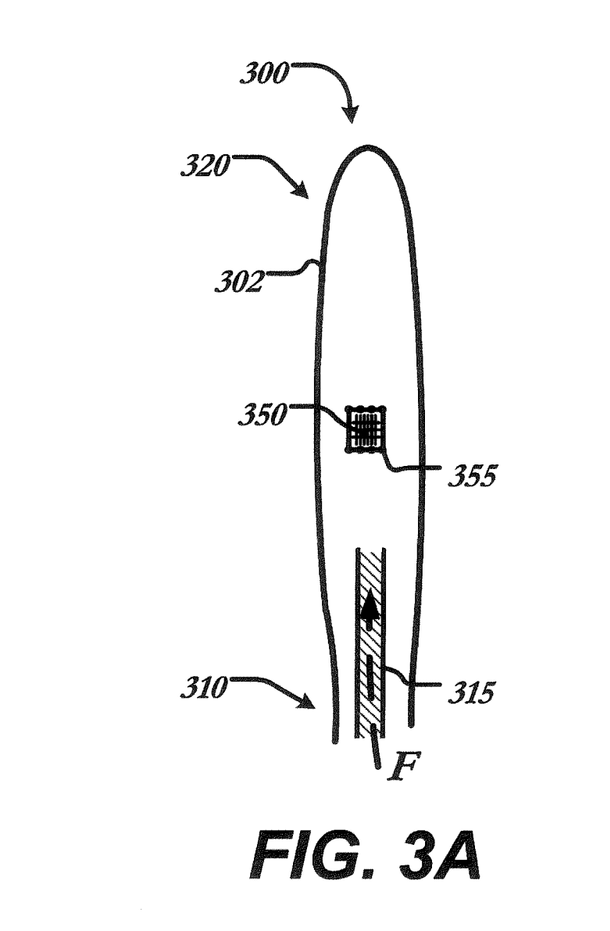
FIG. 3A is a side view of an expandable balloon having a microelectromechanical sensor according to a first embodiment of the present invention.
Figure 3B:
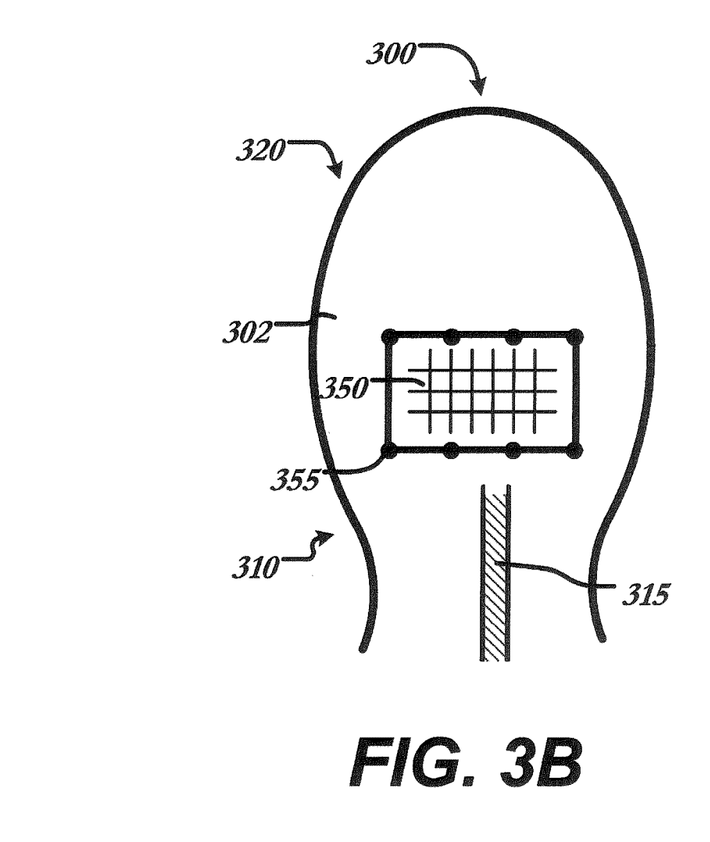
FIG. 3B is a side view of the balloon of FIG. 3A after inflation.

FIG. 3 illustrates a valve sizing device 300 according to a first embodiment of the present invention. The valve sizing device 300 includes an expandable balloon 302 and a sensor 350 attached to the wall of the balloon 302. The balloon 302 may have a proximal end 310 and a distal end 320, and may be wholly or partly formed of PET, Nylon, polyurethane, a thermoplastic elastomer or combinations thereof. Sensor 350 may be a microelectromechanical sensor and may include but is not limited to sensors capable of measuring capacitance, piezoelectricity or any other suitable parameter. Sensor 350 may also include a flexible tactile microelectromechanical sensor.

Sensor 350 may be embedded within balloon 302 or coupled to the balloon in any suitable manner and at various points on the wall of the balloon. For example, sensor 350 may be coupled to balloon 302 at junctions 355 using an adhesive or other suitable method. Deformation of balloon 302 may cause a corresponding deformation in sensor 350 and thus the sensor may comply with intravascular geometry. It will be understood that more than one sensor 350 may be coupled to balloon 302 as will be seen in the embodiments described below. For example, two or three sensors 350 may be evenly disposed about the circumference of balloon 302. The sensors 350 may be disposed on the periphery of balloon 302 so that they are capable of contacting body tissue upon inflation of the balloon.

Prior to insertion into a patient, balloon 302 may be folded into the collapsed condition shown in FIG. 3A, for example, using a pleat fold or a T-fold. Once the sizing device 300 has been placed in the desired position within the patient, a fluid may be injected into the balloon 302 to expand the balloon to a suitable diameter. Specifically, balloon 302 may include a conduit 315 for carrying a fluid from a fluid source (not shown) to the interior of the balloon. Inflation fluids may be a gas, such as helium or carbon dioxide, or a liquid, such as saline.

In its fully expanded condition, balloon 302 may have a generally circular cross-section, although other cross-sectional shapes are contemplated, including triangular, rectangular, trapezoidal, elliptical, curved, and other polygonal and non-polygonal shapes. When fully expanded balloon 302 has a cross-sectional size that is greater than the cross-sectional size of aortic sinus. This will ensure that balloon 302 fully contacts the native tissue around substantially the entirety of the sinus so that the size of the sinus can be determined accurately.

By knowing the material properties of the balloon 302 (e.g., elasticity, etc.) and the volume of fluid being introduced through fluid conduit 315, the diameter or the cross-section of balloon 302 may be estimated. In at least some examples, the balloon 302 is inflated in vitro using known volumes of fluid and a plot is generated to establish the relationship between volume of fluid and cross-section of the balloon. This may be done by the manufacturer prior to shipping device 300, or by the user at the surgical site. Once this relationship is known, the balloon 302 may be collapsed and inserted in vivo at the target site. A volume of fluid may be introduced and the diameter of the native valve annulus estimated based on the pre-established relationship. In addition, as the balloon 302 expands at the target site, sensors 350 begin to contact surrounding tissue and measure the forces generated by this contact.

Figure 4:
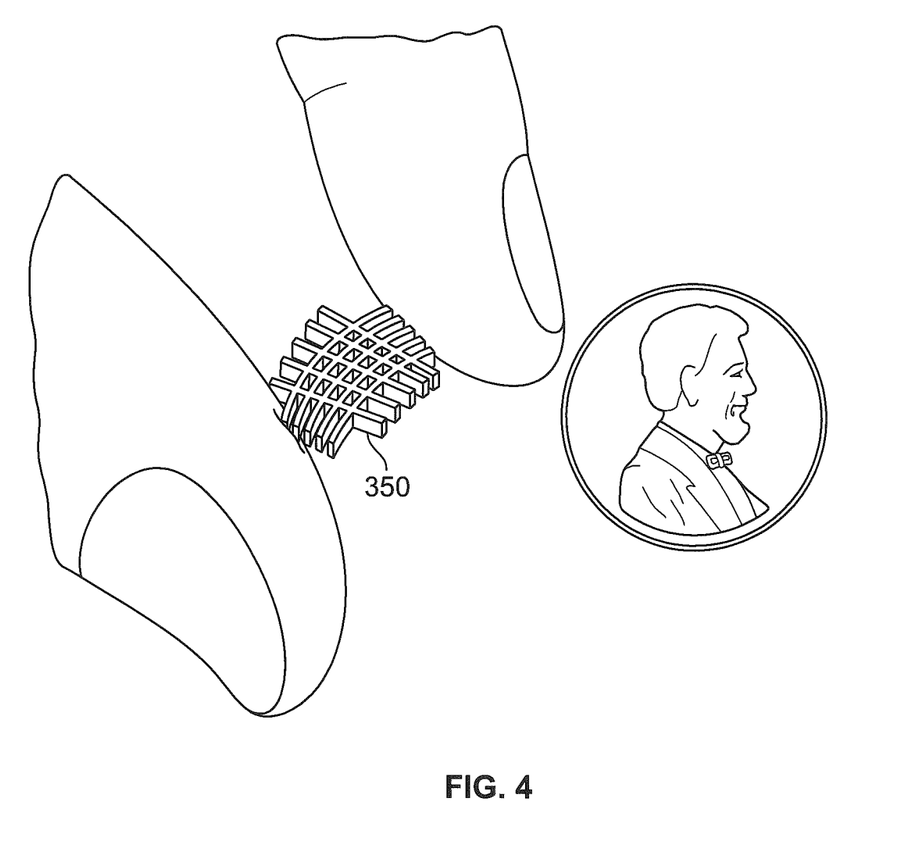
FIG. 4 is a perspective view of a microelectromechanical sensor.

FIG. 4 illustrates one possible configuration of a suitable microelectromechanical sensor 350. As seen in FIG. 4, sensor 350 may be flexible and deformable in order to collect information about size, shape and calcification of the native aortic valve. In that regard, sensor 350 may be fashioned from a fabric or flexible polymer such as polydimethylsiloxane or a polyimide having a pair of electrodes as will be described in greater detail with reference to FIGS. 5B and 5C.

Figure 5A:
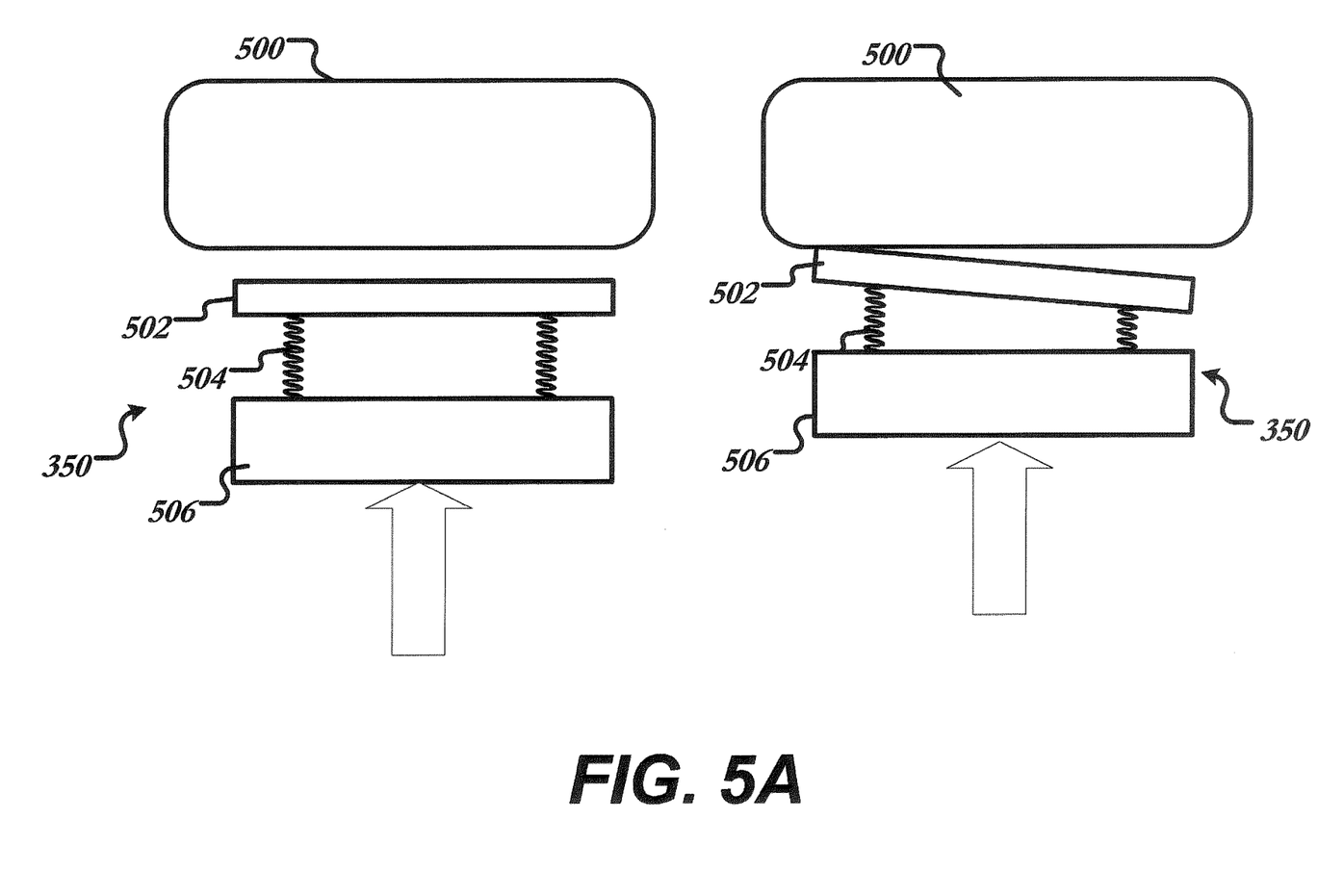
FIG. 5A is a highly schematic view illustrating the sensing of a microelectromechanical sensor.

FIG. 5A is a schematic view illustrating the use of sensor 350 being used to measure calcification of tissue. Sensor 350 may include a contacting member 502, a pair of springs 504 and a base layer 506. Springs 504 may be connected to both the contacting member 502 and the base layer 506 and disposed between the two. It will be understood that springs 504 may be formed of springs having different spring constants. The sensor 350 may be positioned near target tissue 500 to measure the stiffness of the tissue. As can be appreciated from FIG. 5A, sensor 350 may be brought in contact with tissue 500, with contacting member 502 abutting the tissue. As the sensor 350 is gradually advanced, springs 504 begin to flex. By examining the force exerted on springs 504 and the displacement of the springs, the stiffness of tissue 500 may be determined. This stiffness measurement may then be used in turn to analyze the extent of calcification of the tissue and to choose the appropriate prosthetic heart valve for implanting in the patient.

Figure 5B:
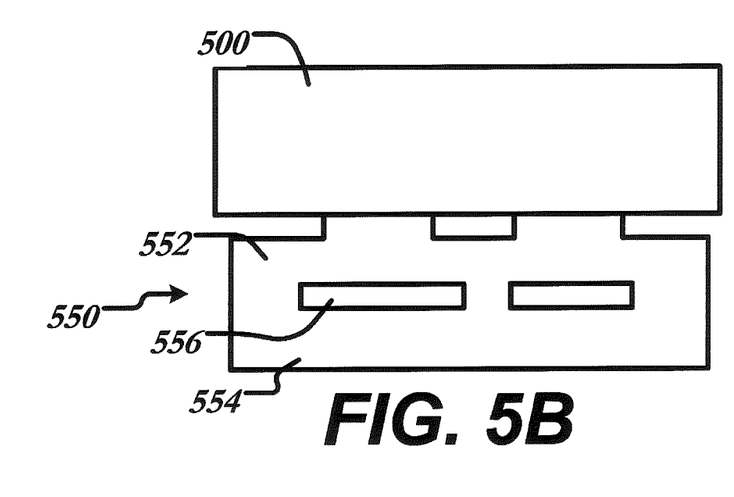
FIGS. 5B and 5C illustrate microelectromechanical sensor formed of a capacitative pair.
Figure 5C:
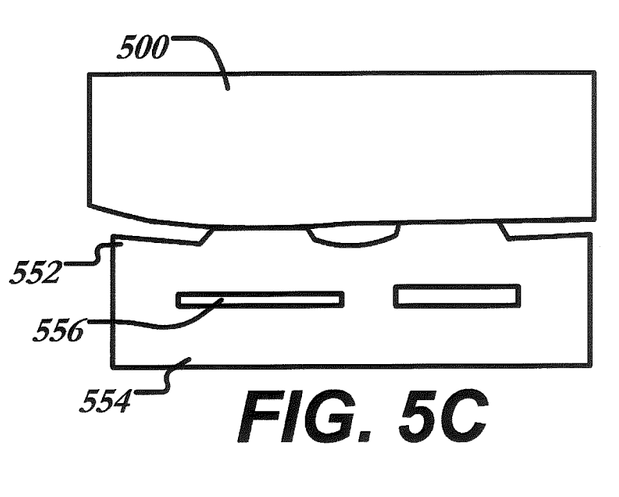

This sensing concept may be implemented using a capacitor pair as shown in FIGS. 5B and 5C. As shown in these figures, capacitor 550 includes a top electrode 552, a bottom electrode 554 and an air gap 556. As seen in FIG. 5B, air gaps 556 are formed of varying sizes analogous to the different springs discussed above with reference to FIG. 5A. When the sensor is contacted by tissue 500 as seen in FIG. 5B, relative deflection may be precisely measured by the capacitive change of each element as shown in FIG. 5C.

The following will describe the use of sizing device 300 for sizing, positioning and selecting an appropriate prosthetic heart valve. As an initial step, the balloon 302 of the sizing device 300 may first be expanded in vitro to determine the relationship between fluid volume and balloon diameter, as described above. The valve sizing device 300 may then be inserted into the patient in the collapsed condition and advanced to the desired site for valve replacement. For example, for transfemoral insertion, the sizing device 300 may be inserted into the patient's femoral artery and advanced intravascularly to the descending aorta and the site of the native aortic valve. If the sizing device 300 includes echogenic materials, it may be guided to the appropriate position using the assistance of three-dimensional echocardiography to visualize the sizing device 300 within the patient.

Once sizing device 300 has reached the desired site of measurement, the balloon 302 may be inflated to assume an expanded shape by introducing a fluid through the fluid conduit 315. With balloon 302 in its expanded condition, measurements relating to the annulus diameter and/or calcification may be made using sensor 350. After sufficient data has been collected or when the collected data shows that the walls of the native sinus have been reached, the balloon 302 may be collapsed by removing the fluid therefrom and the sizing device 300 may be removed from the patient's body. The collected data may then be used to select the appropriate prosthetic valve size and position, and the prosthetic valve may be deployed and anchored at the selected site using any manner known in the art. While the operation of the sizing device 300 of FIG. 3 has been described, it will be understood that other embodiments described below may be implemented in a similar manner.

Figure 6A:
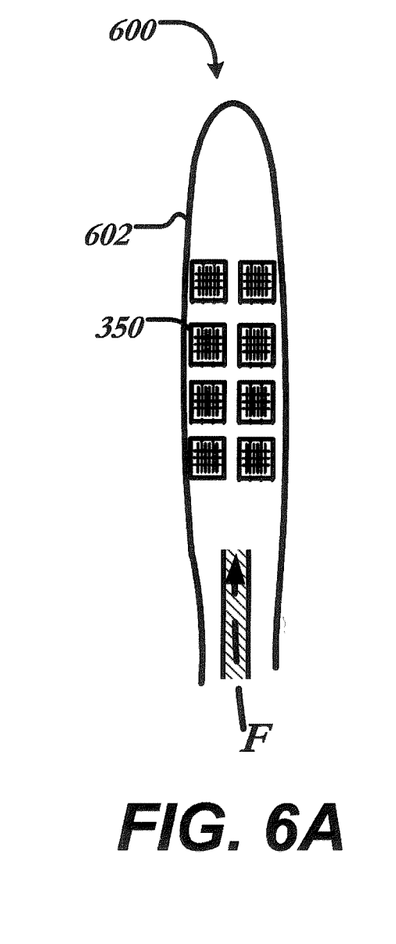
FIG. 6A is a side view of a collapsed balloon having microelectromechanical sensors according to a second embodiment of the present invention.
Figure 6B:
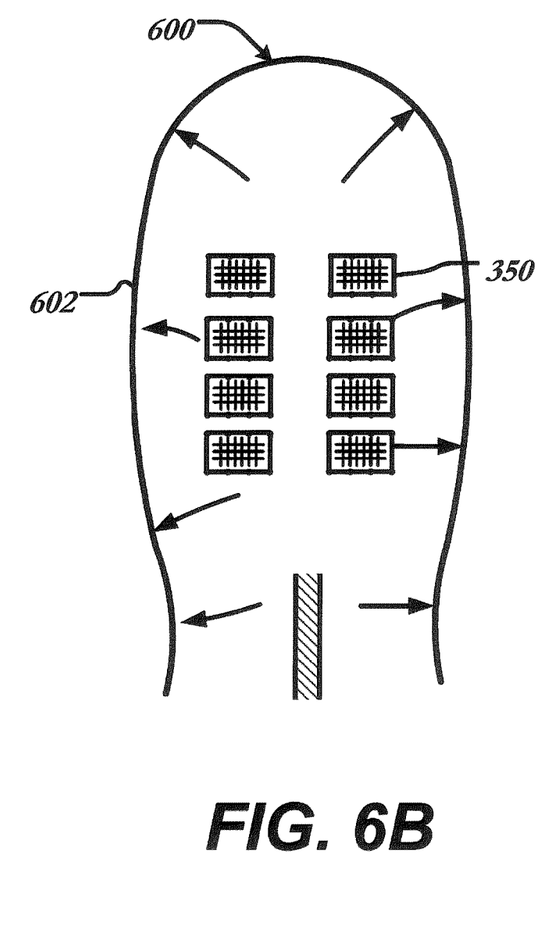
FIG. 6B is a side view of the balloon of FIG. 6A after inflation.

FIG. 6A illustrates a second embodiment of a valve sizing device 600, similar to valve sizing device 300 of FIG. 3, but having a plurality of sensors 350 attached to the wall of a balloon 602. FIG. 6B illustrates the sizing device 600 of FIG. 6A in its expanded condition. FIGS. 6A and 6B illustrate six sensors 350 coupled to balloon 602. It will be understood, however, that any number of sensors 350, such as two, three, four, six or more sensors 350, may be disposed on balloon 602. As previously discussed, sensors 350 may be flexible and pliable so that they are capable of accommodating expansion of balloon 602.

Figure 7:
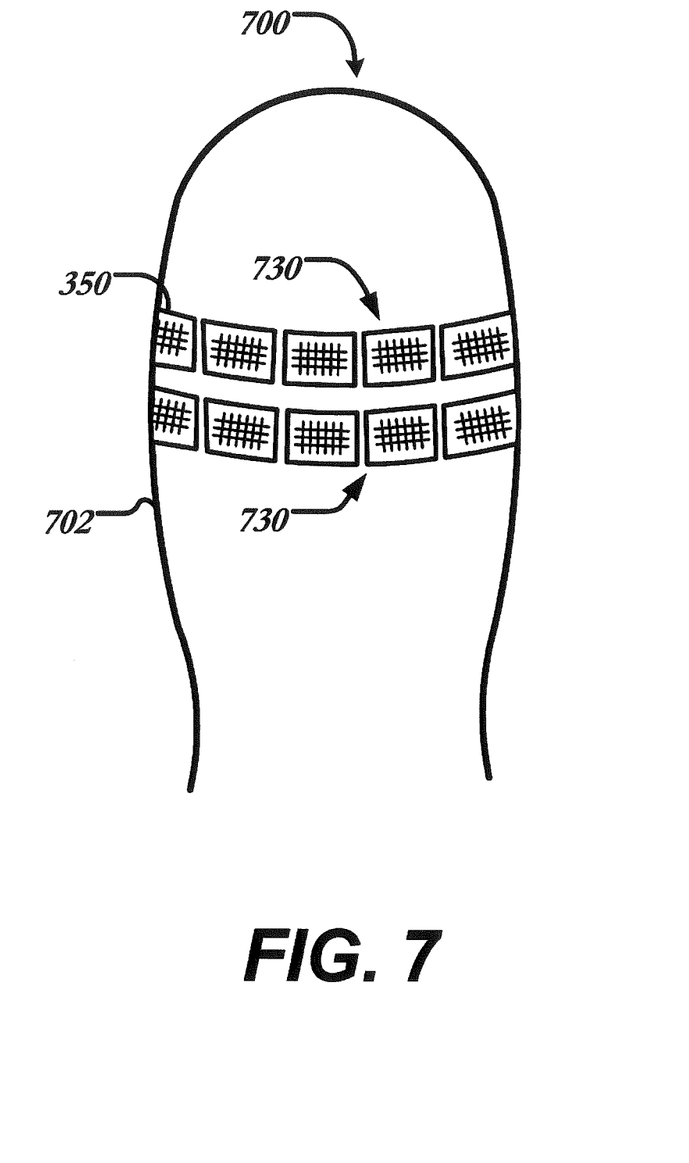
FIG. 7 is a side view of an inflatable balloon having microelectromechanical sensors arranged in rings according to a third embodiment of the present invention.

FIG. 7 is a side view of a valve sizing device 700 according to a third embodiment of the present invention, including an inflatable balloon 702 having a plurality of sensors 350 attached thereto. As illustrated in FIG. 7, the plurality of sensors 350 are arranged about the periphery of balloon 702. Specifically, sensors 350 may be arranged in rings 730 around the circumference of balloon 702. By arranging the plurality of sensors 350 in rings 730, the forces applied to the balloon 702 at any point around the circumference of the balloon may be measured. Although valve sizing device 700 includes two rings 730, it will be understood that sensors 350 may be arranged in any number of rings around the circumference of balloon 702.

Figure 8:
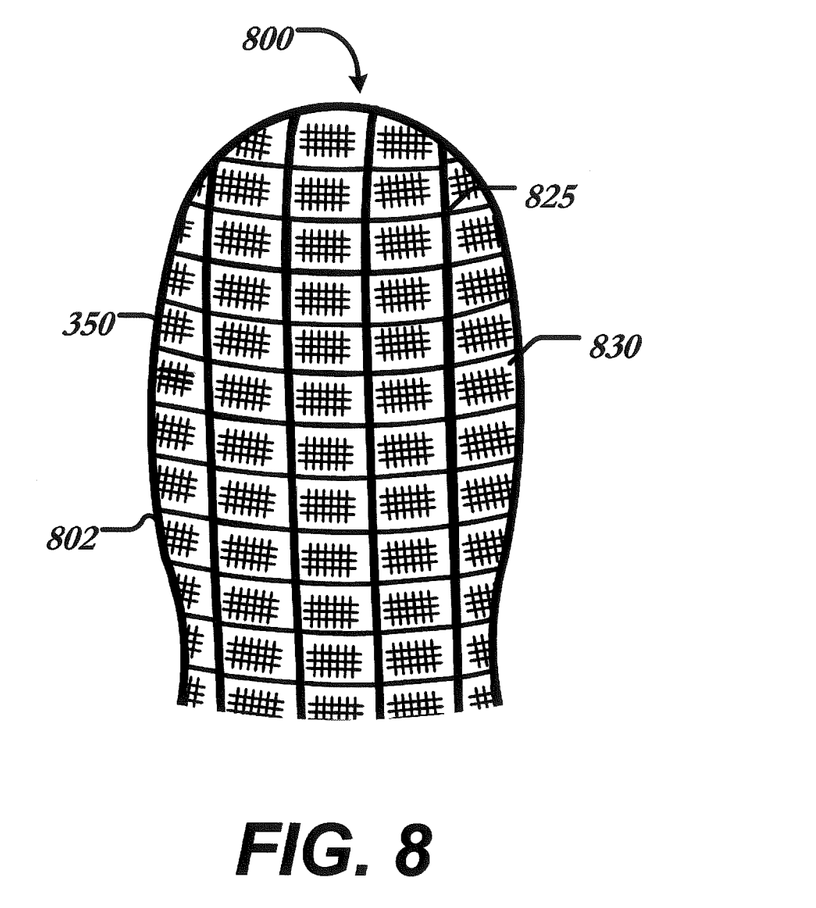
FIG. 8 is a side view of an inflatable balloon formed of microelectromechanical sensors according to a fourth embodiment of the present invention.

FIG. 8 illustrates a fourth embodiment of a valve sizing device 800 including an inflatable balloon 802 formed of microelectromechanical sensors 350. As will be appreciated from FIG. 8, the balloon 802 may be formed by joining a plurality of sensors 350 to each other along seams 825 extending in both longitudinal and circumferential directions. Each sensor 350 may include a substrate 830 formed of a flexible material, such as rubber, fabric, a polyimide, or polydimethylsiloxane (PDMS). Substrates 830 may be joined together in edge-to-edge fashion along seams 825 to form a balloon 802. The attachment along seams 825 may be made such that fluid is not able to pass between substrates.

In this manner, fluid can be introduced into balloon 802 for inflation through a fluid conduit (not shown) or any other suitable means. It will be understood that combinations of these embodiments may be possible. For example, a balloon may only be partially formed of sensors to reduce cost.

It will also be noted that while the inventions herein are predominately described in connection with the replacement of a tricuspid valve, the inventions are equally applicable to the replacement of other valves, including a bicuspid valve, such as the mitral valve. Moreover, the stent could have different shapes, such as a flared or conical annulus section, a less-bulbous aortic section, and the like, and a differently shaped transition section.

Moreover, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A sizing device for a collapsible prosthetic heart valve, the sizing device comprising:
a plurality of microelectromechanical sensors, each of the plurality of microelectromechanical sensors being disposed on a flexible substrate, having a top electrode having a contacting surface, a bottom electrode, and an air gap disposed between the top electrode and the bottom electrode, the top electrode and the bottom electrode being deflectable relative to one another, and configured to measure capacitive changes to determine a relative deflection between the top electrode and the bottom electrode, each of the plurality of microelectromechanical sensors being capable of independently measuring, with respect to others, a stiffness value of a native valve annulus by pressing against portions of the native valve annulus with the contacting surface, each flexible substrate being joined edge-to-edge along seams with adjacent substrates to form a collapsible and expandable balloon.

2. The device of claim 1, further comprising a conduit in fluid communication with the inside of the balloon for delivering a fluid to inflate the balloon.

3. The device of claim 2, wherein the balloon comprises at least one of PET, Nylon, polyurethane or a thermoplastic elastomer.

4. The device of claim 1, wherein the flexible substrate includes a polymer.

5. The device of claim 4, wherein the polymer includes polydimethylsiloxane.

6. The device of claim 4, wherein the polymer includes a polyimide.

7. The device of claim 1, wherein the flexible substrate includes a fabric.

8. The device of claim 1, wherein the plurality of microelectromechanical sensors are in contact with one another.

9. A sizing device for a collapsible prosthetic heart valve, the sizing device comprising a plurality of microelectromechanical sensors, each of the plurality of microelectromechanical sensors being disposed on a flexible substrate, the flexible substrate being directly coupled edge-to-edge along seams to adjacent substrates to form a collapsible and expandable balloon, each of the plurality of microelectromechanical sensors having a top electrode having a contacting surface, a bottom electrode, and an air gap disposed between the top electrode and the bottom electrode, the top electrode and the bottom electrode being deflectable relative to one another, and being capable of independently measuring, with respect to others, a property of tissue.

10. The device of claim 9, wherein each of the plurality of microelectromechanical sensors is capable of measuring data relating to native valve annulus diameter.

11. The device of claim 9, wherein each of the plurality of microelectromechanical sensors is capable of measuring data relating to the extent of calcification of tissue.

* * * * *